United States Patent
Plante et al.

(10) Patent No.: US 6,874,446 B2
(45) Date of Patent: Apr. 5, 2005

(54) ANIMAL BRUSHES

(75) Inventors: Robin Plante, Sainte-Barbe (CA); Paul Dery, Montreal (CA)

(73) Assignee: Rolf C. Hagen, Inc., Montreal (CA)

( * ) Notice: Subject to any disclaimer, the term of this patent is extended or adjusted under 35 U.S.C. 154(b) by 0 days.

(21) Appl. No.: 10/423,246

(22) Filed: Apr. 25, 2003

(65) Prior Publication Data

US 2003/0209210 A1 Nov. 13, 2003

Related U.S. Application Data

(60) Provisional application No. 60/378,539, filed on May 7, 2002.

(51) Int. Cl.[7] .......................... A01K 13/00; A46B 9/06; A45D 24/16
(52) U.S. Cl. ..................... 119/612; 119/615; 15/207.2; 130/120
(58) Field of Search ...................... 15/207.2; D04/119, D04/134, 136; 119/611–620, 625, 631, 664; 132/120

(56) References Cited

U.S. PATENT DOCUMENTS

| | | | | |
|---|---|---|---|---|
| 202,161 A | * | 4/1878 | Finley | 119/613 |
| 819,444 A | * | 5/1906 | Monroe | 132/212 |
| 823,464 A | * | 6/1906 | Eggers | 132/103 |
| 1,401,576 A | * | 12/1921 | Babirad | 132/121 |
| 1,818,495 A | * | 8/1931 | Midgley | 119/632 |
| D96,599 S | * | 8/1935 | Gilbert et al. | D4/134 |
| 2,238,603 A | * | 4/1941 | Runnels | 132/120 |
| 2,464,321 A | * | 3/1949 | Konczal | 15/167.1 |
| 2,610,637 A | * | 9/1952 | Fuentes | 132/120 |
| 2,663,303 A | * | 12/1953 | Winchester et al. | 132/120 |
| D197,327 S | * | 1/1964 | Murphy | D4/119 |
| 3,133,546 A | * | 5/1964 | Dent | 132/120 |
| 3,180,342 A | * | 4/1965 | Dietsche | 132/120 |
| 3,199,139 A | * | 8/1965 | Vallis | 401/22 |
| D237,245 S | * | 10/1975 | Smyth | D8/6 |
| 4,856,541 A | * | 8/1989 | Kellett et al. | 132/110 |
| 4,970,990 A | * | 11/1990 | Wilhelmi | 119/601 |
| 5,072,479 A | * | 12/1991 | Van Niekerk | 15/111 |
| 5,267,528 A | * | 12/1993 | Murieen, Sr. | 119/628 |
| 5,503,109 A | * | 4/1996 | Sporn | 119/633 |
| D372,128 S | * | 7/1996 | Beach et al. | D4/116 |
| 5,819,758 A | * | 10/1998 | Sohler | 132/121 |
| D409,461 S | * | 5/1999 | Kiefer | D8/13 |
| 5,930,862 A | * | 8/1999 | Garrett | 15/200 |
| D425,707 S | * | 5/2000 | Olsson | D4/119 |
| D443,142 S | * | 6/2001 | Harada | D4/104 |
| D451,680 S | * | 12/2001 | Holmes et al. | D4/136 |
| 6,341,611 B1 | * | 1/2002 | Nakamura | 132/120 |
| 6,367,422 B1 | * | 4/2002 | Wilhelmi | 119/625 |

FOREIGN PATENT DOCUMENTS

JP            11070019 A    *   3/1999            A46B/9/06

* cited by examiner

*Primary Examiner*—Teri Pham Luu
*Assistant Examiner*—Bret Hayes
(74) *Attorney, Agent, or Firm*—Wolf, Greenfield & Sacks, P.C.

(57) ABSTRACT

A light weight animal grooming brush has a contoured gripping handle and head attached to the handle having a working surface carrying grooming implements such as tines. The working surface is contoured and is disposed at an angle to the handle.

9 Claims, 4 Drawing Sheets

ANIMAL BRUSHES

RELATED APPLICATIONS

This application claims priority under 35 U.S.C. § 119(e) to U.S. Provisional Application Ser. No. 60/378,539, entitled "ANIMAL BRUSHES," filed on May 7, 2002, which is herein incorporated by reference in its entirety.

BACKGROUND OF INVENTION

1. Field of Invention

This invention relates to animal grooming products and more particularly is a new grooming brush and comb combination that is easy to use and provides maximum grooming effectiveness.

2. Summary of the Invention

To achieve those goals, the brush assembly is lightweight, has a comfortably contoured handle, has a convex working surface that is more effective than flat brush surfaces commonly used, includes a heavy duty rake which is particularly effective for heavily haired animals, has a large area of very thin wire tines for surface and middle depth combing of animal hairs and that retains the hairs that become loose during combing and provides an angular relationship between the handle and brush head that avoids unnecessary stress on the hand muscles or wrist ligaments from repetitive action that occurs when grooming an animal. The grooming tool also has a convenient storage compartment in the handle for a comb used for fine grooming. The advantages of the present invention will be better understood and appreciated from the following detailed description.

Each of these aspects of the invention independently contributes to the performance of the brush and comb assembly, and the invention is not limited to such a device that has all of them.

BRIEF DESCRIPTION OF DRAWINGS

The accompanying drawings, are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
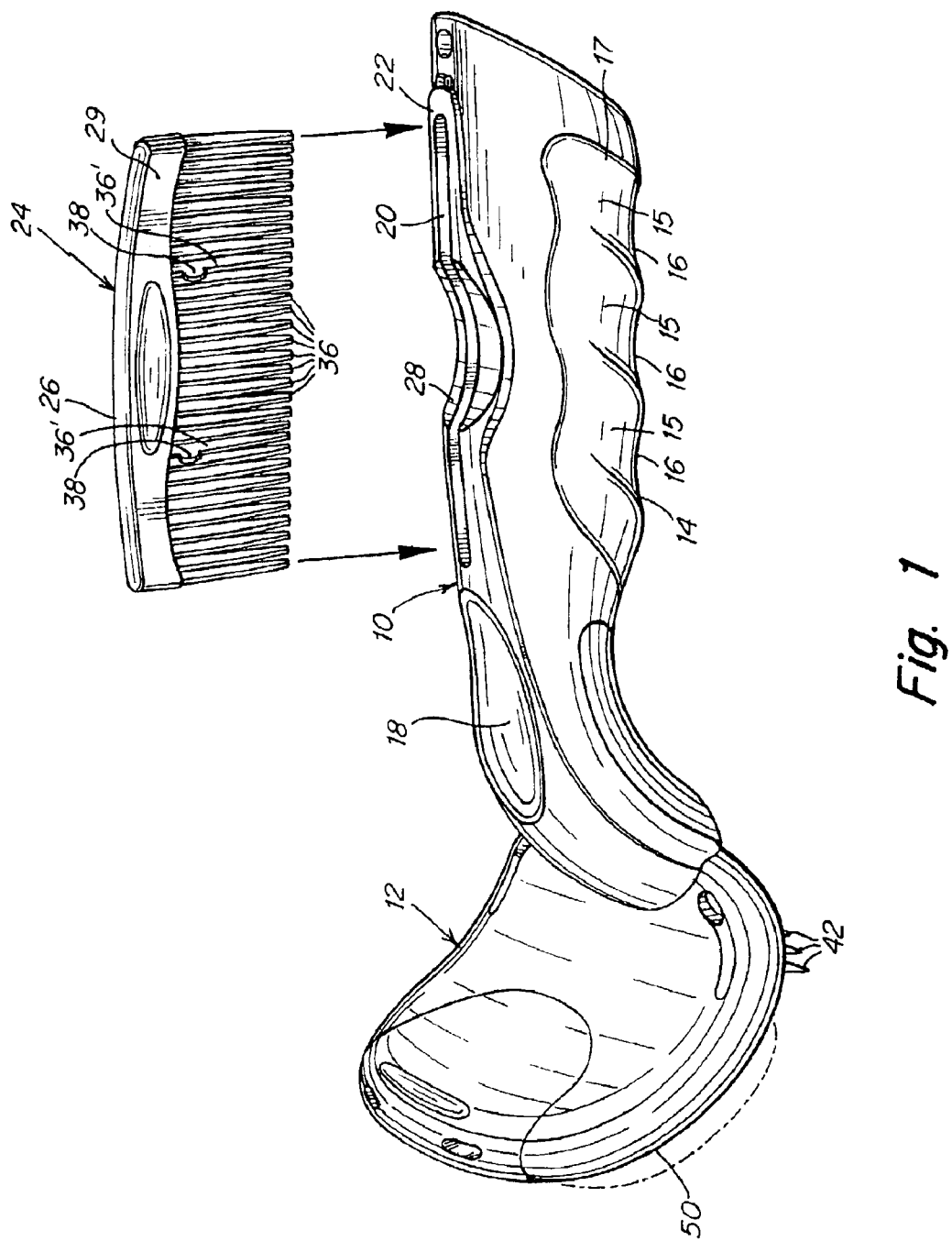
FIG. 1 is an exploded perspective view of the animal grooming brush assembly of this invention with its comb removed from the assembly handle.
Figure 2:
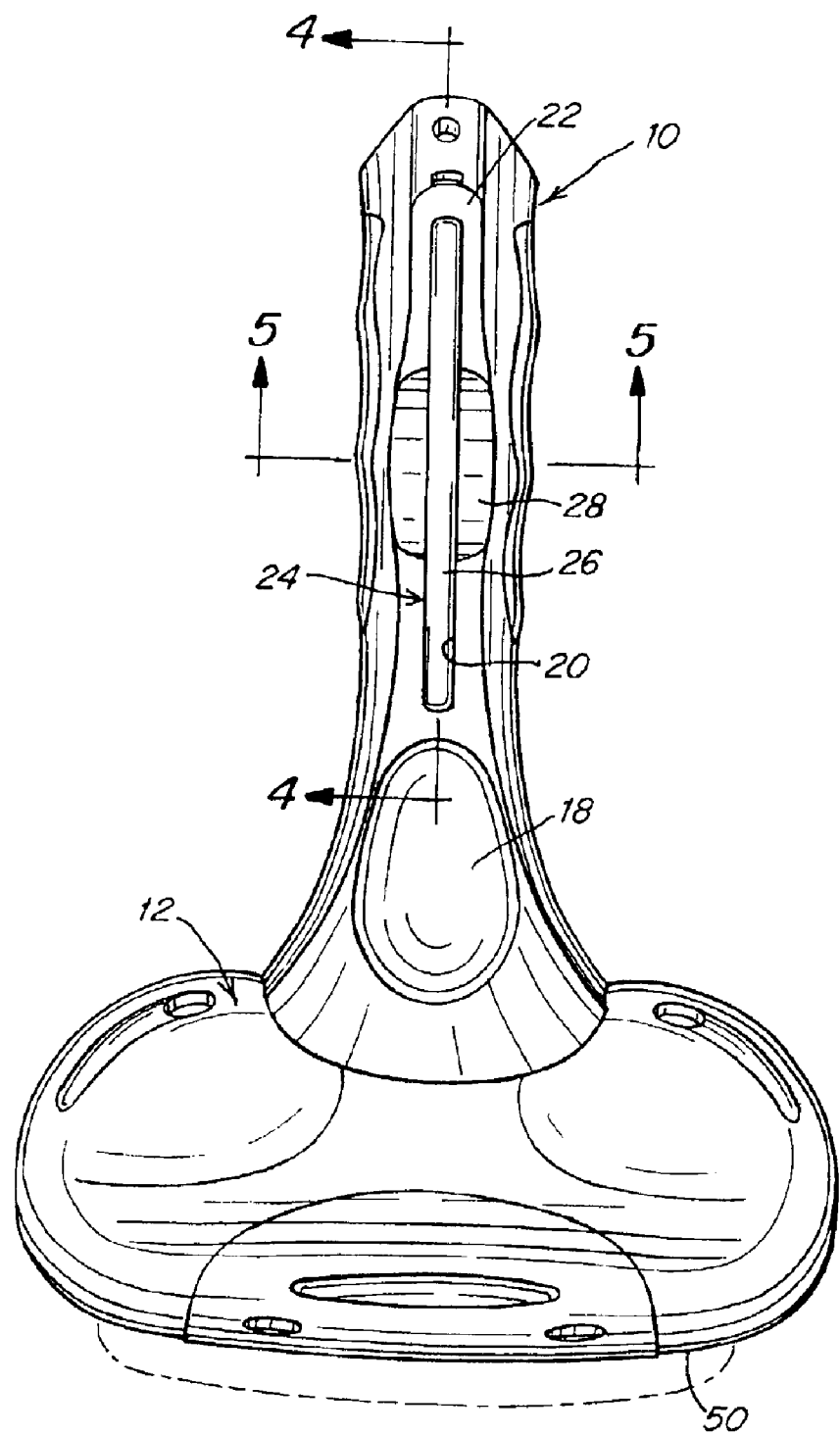
FIG. 2 is a top plan view of the grooming brush assembly with the comb disposed in the slot in the handle.
Figure 3:
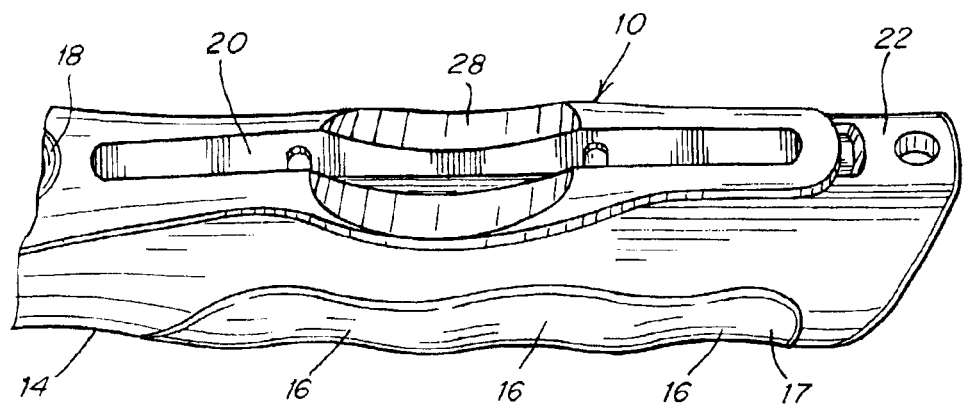
FIG. 3 is an enlarged perspective view of the handle of the assembly and showing details of the comb slot.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Figure 5:
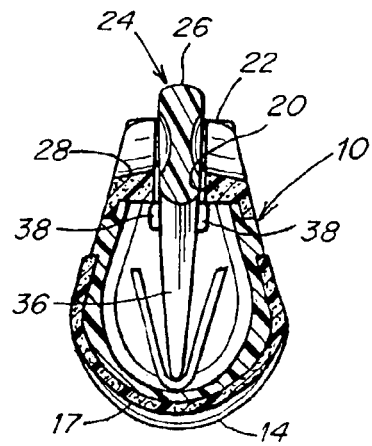
FIG. 5 is a cross-sectional view of the handle and comb taken along section line 5—5 in FIG. 2.

The grooming brush assembly of the present invention includes a handle 10 and brush head 12 that may be separately formed and connected together or alternatively formed as a unitary structure. In accordance with one aspect of the invention, the handle 10 preferably is contoured as shown in FIGS. 1–3 and 7 so as to provide improved comfort and enhanced gripping of the assembly. The lower surface 14 of the handle is contoured as shown at 16 and the special finger contours 15 extend upwardly along the sides of the handle. For further comfort, the handle preferably is over-molded of elastomeric plastic (see FIGS. 1, 3 and 5 at 17) on a comparatively rigid handle frame of polypropylene or other suitable material. A thumb depression 18 preferably is also provided on the upper surface 22 of the handle near the head end to further enhance the gripping of the handle.

Figure 4:
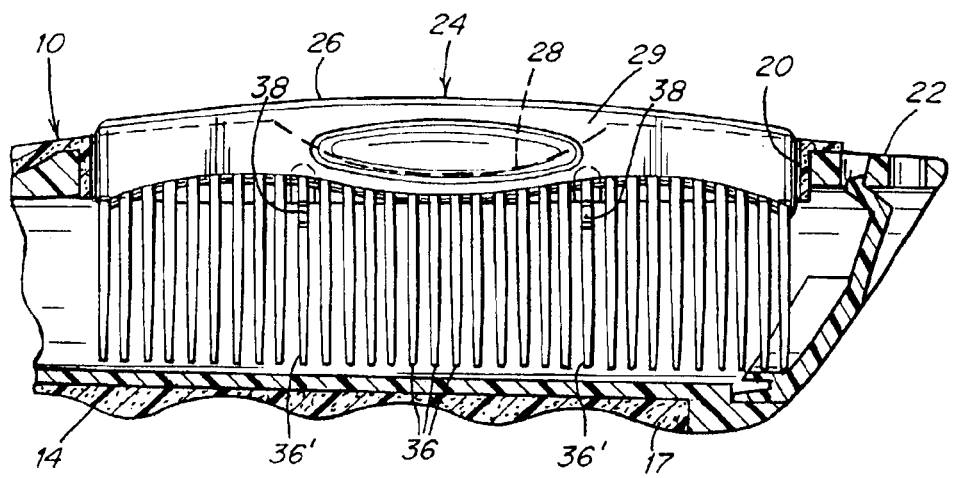
FIG. 4 is a fragmentary cross-sectional view of the handle and showing the comb in place in the handle slot, taken along section line 4—4 in FIG. 2.

The handle 10 in the embodiment illustrated includes an elongated slot 20 open in its upper surface 22, which is sized to receive a grooming comb 24 as suggested in FIG. 1 and shown in FIG. 4. When the comb is placed in the slot 20, the upper edge 26 of the comb with its hand grip 29 extends very slightly out of the slot 20 so as not to interfere with the gripping of the handle. A shallow recess 28 is also provided in the upper surface of the brush handle 10 and extends across the top of the slot 20 so as to expose a portion of the sides of the comb hand grip 29 to facilitate insertion and removal of the comb to and from the slot. To assist in retaining the comb 24 in the slot 20 so that it will not accidentally fall from it and become lost, a few of the tines 36[1] identified collectively at 36 bulge outwardly as shown at 38 (see FIG. 5) so as to provide a catch to bear against the sides of the slot and thereby frictionally engage the slot walls to releasably retain the comb in it. Depending upon the shape and size of the handle, slot 20 may alternatively be provided in the sides or bottom surface of the handle.

Figure 6:
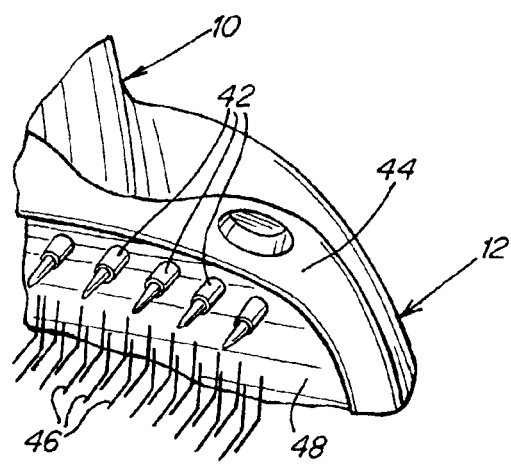
FIG. 6 is a fragmentary perspective view of the head of the assembly viewed from beneath the brush head and showing a portion of the heavier wire tines and several fine wire combing tines in accordance with this invention.
Figure 7:
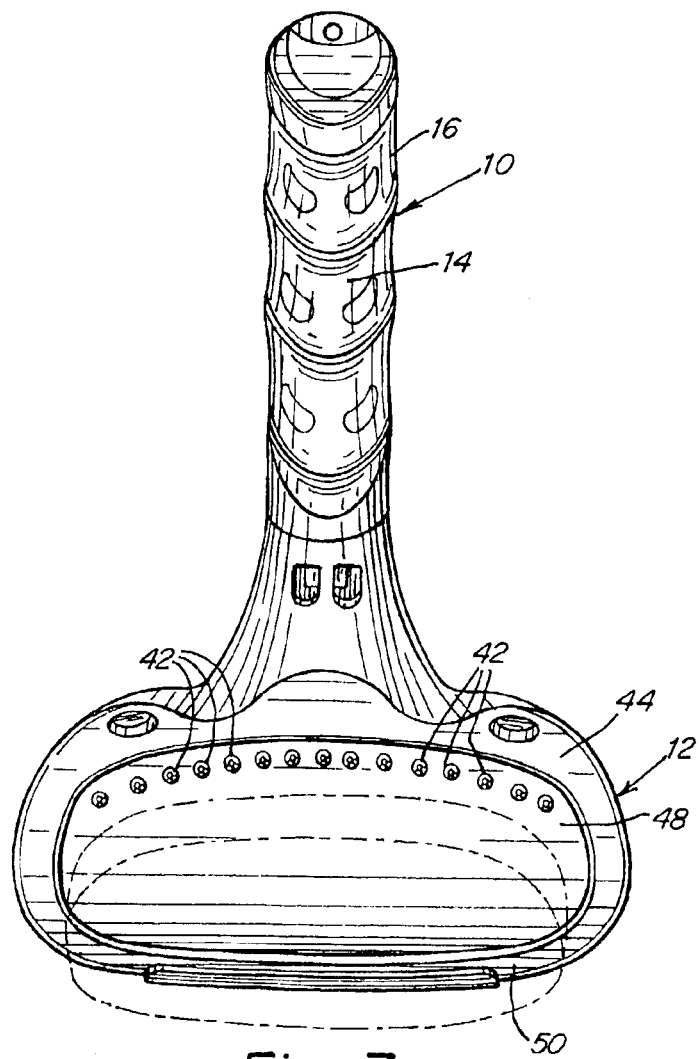
FIG. 7 is a bottom view of the animal grooming brush assembly; with the area of the fine wires of the brush suggested in broken lines.

The head 12 of the brush assembly as suggested in FIGS. 6 and 7 carries an array of heavy comb tines 42 (collectively a rake) on the bottom of the head across the heal 44 thereof for deep "raking" of the heavy hair of an animal. In addition, the head carries a dense array of fine wire tines 46 for surface and middle depth combing of the hair of the animal. The heavy tines 42 and the fine wire tines 46 are carried on a pad 48 that is mounted on the head. The pad with tines 42 and 46 may or may not be removable from the head. The fine tines 46 will retain detached animal hairs so that they will not scatter about the area where the animal is being groomed. The pad may come in a variety of forms carrying either or both of the tines. The grooming surface (lower surface) 50 may be bowed about an axis perpendicular to the longitudinal center line of the handle to provide a convex working surface as shown in FIG. 1 to facilitate drawing the brush over the animal, and the head 12 is disposed at an angle with respect to the handle to enhance the comfort and convenience of using the brush assembly. The axis of the head may also be parallel to the plane of the top of the handle.

The present invention provides many advantages for the user. One aspect of this invention is that it is light weight. Another is that the brush is easy to maneuver and manipulate. Furthermore, it does not cause stress on the hand muscles or wrist ligaments that otherwise results from repetitive action that occurs when grooming an animal. Yet another aspect of the invention is the convenient location of a separate comb that may be helpful particularly for special grooming operations.

The brush assembly may be made in a variety of sizes so as to be suitable for grooming both small and large animals such as both cats and dogs. When used for small animals, the pad would normally carry only the finer combing tines 46 while for larger animals the pad used would beneficially include both the heavy and the fine tines. As yet another alternative, the pad may be free of tines, but rather carry merely a rubber-like surface for grooming the animal coat.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only and the scope of the invention is to be determined by the appended claims and their equivalents.

What is claimed is:

1. An animal brush assembly comprising a brush head having a convex working surface curved in one direction and relatively flat in a second direction generally perpendicular to said one direction, said head having a heel along a side thereof extending in said second direction, a handle secured to the brush head at the heel and perpendicular to the second direction, and an array of relatively heavy tines on the working surface of the head confined to an area adjacent to and substantially coextensive with the heel for deep raking of the heavier hair of an animal and a second array of relatively fine tines on the working surface remote from the heel for surface and middle depth combing of the hair and for collecting loose hair of the animal.

2. The animal brush assembly of claim 1 wherein the relatively heavy tines are disposed in a row generally perpendicular to the handle.

3. The animal brush of claim 2, wherein the relatively fine tines extend over a major portion of the working surface.

4. The animal brush assembly of claim 3 wherein a slot is formed in the handle and an animal grooming comb is removably mounted in said slot for use independent of the brush.

5. The animal brush assembly of claim 3 wherein the head carries a pad on its working surface, and the heavy and fine tines extend away from the pad.

6. The animal brush assembly of claim 5 wherein the pad is detachably connected to the head, and the heavy and fine tines are carried by the pad.

7. The animal brush assembly of claim 3 wherein the handle has a soft elastomeric surface.

8. The animal brush assembly of claim 7 wherein the handle is contoured for engaging the fingers of the user.

9. The animal brush assembly of claim 8 wherein a slot is formed in the handle and an animal grooming comb is removably mounted in said slot for use independent of the brush.

* * * * *